United States Patent [19]
O'Connor

[11] 3,987,301
[45] Oct. 19, 1976

[54] LIGHT COLLECTION APPARATUS
[75] Inventor: Bartholomew John O'Connor, Dublin, Ireland
[73] Assignee: Talcoma Teoranta, Dublin, Ireland
[22] Filed: Dec. 2, 1975
[21] Appl. No.: 636,869

Related U.S. Application Data
[62] Division of Ser. No. 483,350, June 26, 1974, Pat. No. 3,942,001.

[30] Foreign Application Priority Data
June 27, 1973 Ireland.................................. 488/73
May 14, 1974 Ireland............................... 1036/74

[52] U.S. Cl. ............................ 250/227; 250/223 B; 356/240
[51] Int. Cl.²............................................ G02B 5/14
[58] Field of Search ............ 250/221, 222 R, 223 B, 250/224, 227; 356/240; 209/111.7; 350/96 R, 96 B

[56] References Cited
UNITED STATES PATENTS
3,639,067  2/1972  Stephens ......................... 250/223 B
3,662,883  5/1972  Sager ............................. 209/111.7
3,735,144  5/1973  Babunovic et al. ................. 356/240

Primary Examiner—David C. Nelms
Attorney, Agent, or Firm—Sughrue, Rothwell, Mion, Zinn & Macpeak

[57] ABSTRACT

A light collection apparatus in a machine for detecting the presence of extraneous matter and/or cracks in translucent containers of the type in which a spot beam of light is projected through the container to generate an electrical inspection signal corresponding to the amount of light passing through the container to a light collection apparatus. The light collection apparatus incorporates fiber optic elements so arranged with exposed ends in spaced relation on a platform as to provide an accurate and controllable method of collection.

19 Claims, 5 Drawing Figures

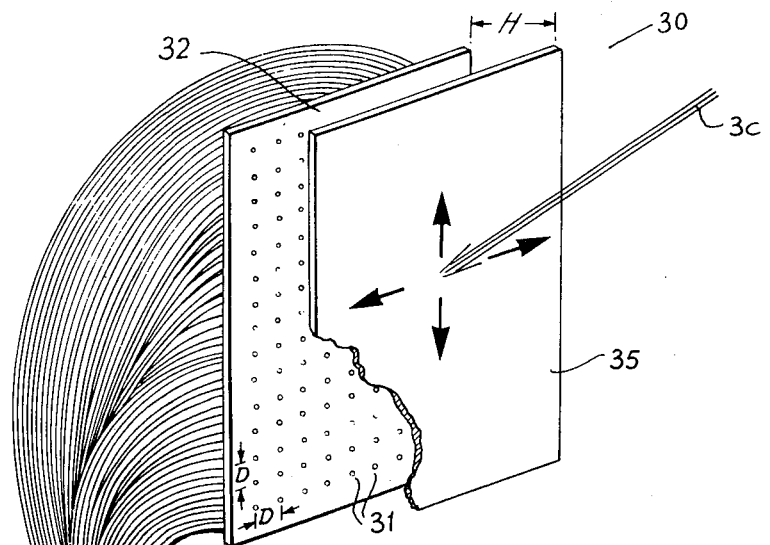
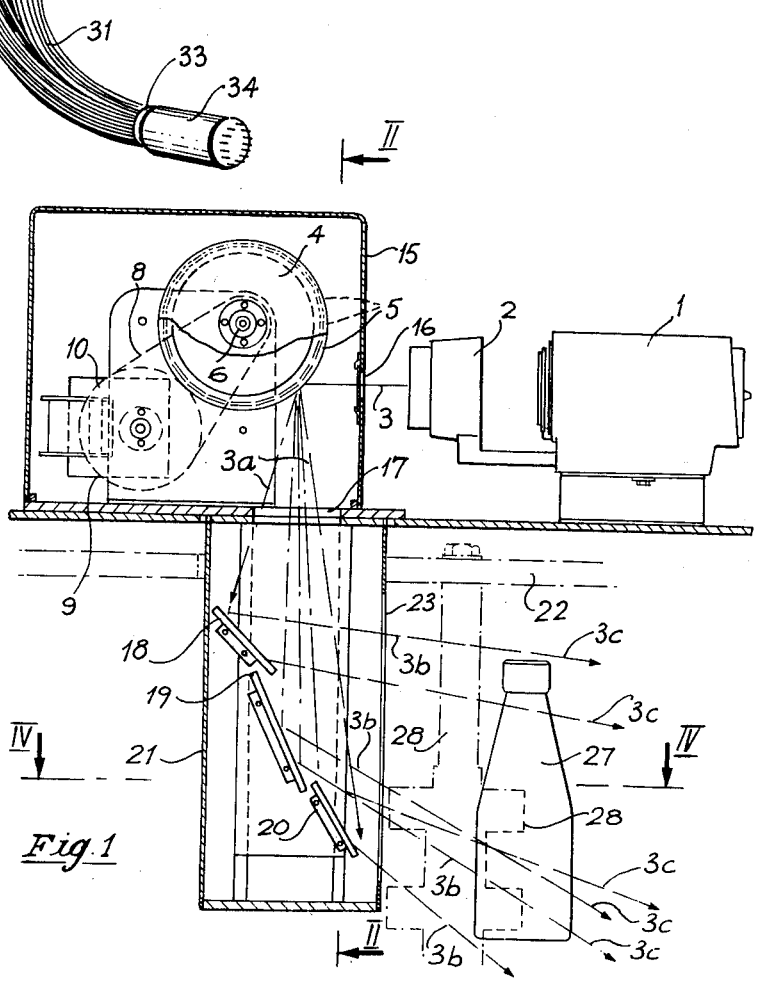
Fig. 5
Fig. 1

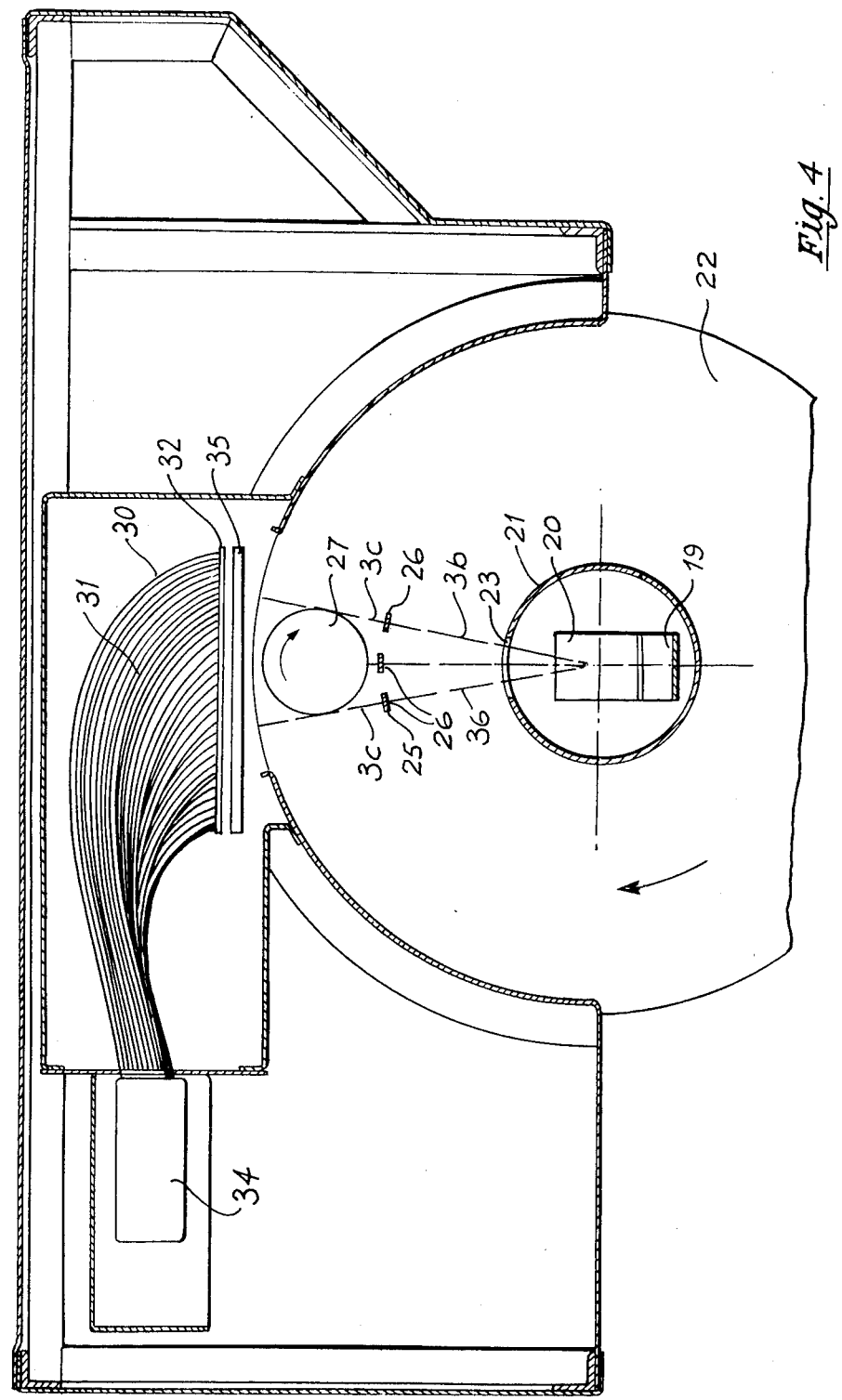

LIGHT COLLECTION APPARATUS

CROSS-REFERENCE TO RELATED APPLICATIONS

This application is a division of my patent application Ser. No. 483,350 filed June 26, 1974 now U.S. Pat. No. 3,942,001.

BACKGROUND OF THE INVENTION

1. Field of the Invention

This invention relates to the inspection of translucent containers for the presence of extraneous matter and-/or cracks and in particular to a light collection apparatus suitable for use with the invention of my co-pending patent application Ser. No. 483,350 filed June 26, 1974.

2. Description of the Prior Art

It is known to use fiber optic elements in bottle inspection and the like apparatus. In German Offenlegungsschrift No. 1,473,749 there is described test and inspection equipment for glass containers in which the light receiving or collection elements of the said apparatus includes a light conducting device formed from a number of glass fiber optic elements. There are however, certain problems in the use of glass fiber optic elements in the manner described in this German Offenlegungsschrift No. 1,473,749. These arise when the area over which light must be collected is large in comparison with the light sensitive area of the photodetector used. It will be appreciated for example that if it is necessary to collect light over an area of for example 20 cms × 50 cms. i.e. 1,000 sq. cms. and to transmit this light to a photodetector such as a photo multiplier tube having a total light sensitive area of maybe 20 sq. cms., it is impossible to do so by means of a bundle of closely packed fiber otpic elements. If the number of fiber optic elements is reduced so as to be compatible with the light sensitive area of the photo multiplier tube the number and spacing of the fiber optic elements in the area 20 cms. by 50 cms.will be inadequate for effective light collection. It will be appreciated that it is essential that all the light impinging on the light collection apparatus be collected. Further it is apparent that the effectiveness of the light collection element of the apparatus is central to the operation of the inspection apparatus. While photo multiplier tubes have the necessary characteristics for use in such inspection machines, they have in general a photo-sensitive area which is of limited size and considerably smaller than the area over which light collection must be provided. If however, fiber optic elements are used in the manner described in German Offenlegungsschrift No. 1,473,749 the problem of the size of the photo-sensitive area of the photo-electric cell is not overcome.

OBJECTS

The present invention is directed therefore towards providing a light collection apparatus of the foregoing type in which the response of the system will be uniform and can be varied. Further, it is an object of the invention to provide a light collection apparatus so that it has graded or locally non-uniform response to the incident light.

DESCRIPTION OF DRAWINGS

FIG. 1 is a side, partially cross-sectional, elevation of an inspection apparatus for use with the light collection apparatus of the invention;

FIG. 4 is a plan cross-sectional view along the lines IV—IV of FIG. 1, and

FIG. 5 is a perspective partially diagramatic view of portion of the light collection apparatus.

DESCRIPTION OF THE PREFERRED EMBODIMENTS

Figure 3:
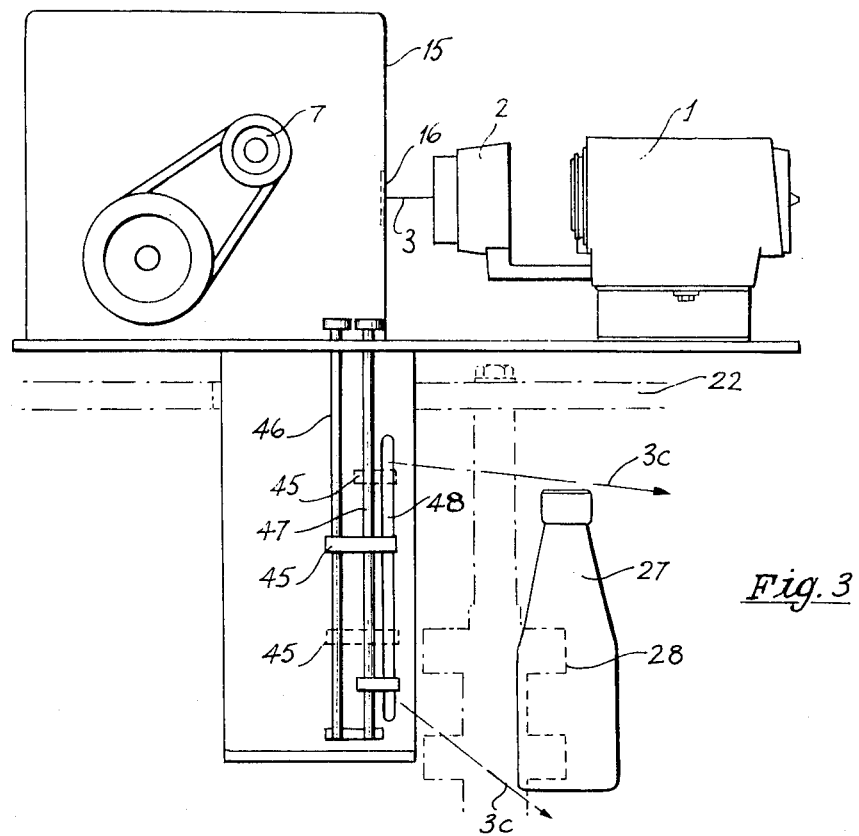
FIG. 3 is a side elevation of portion of the apparatus.
Figure 2:
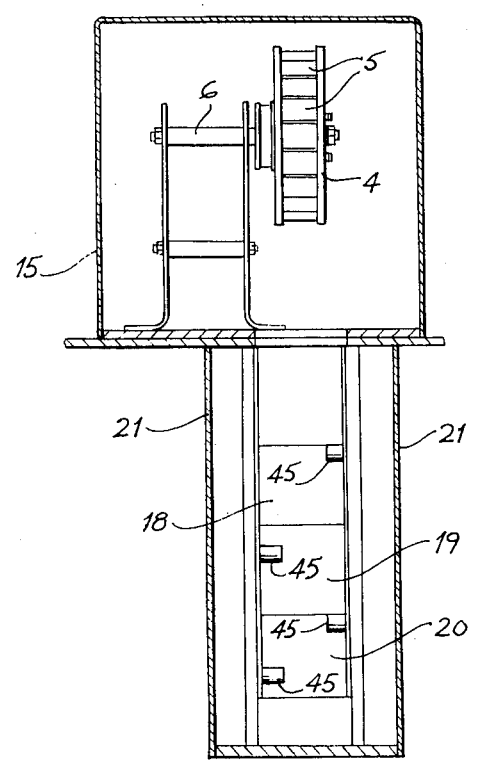
FIG. 2 is a cross-sectional view along the lines II—II of FIG. 1.

Referring to the drawings, and initially to FIGS. 1 to 4 thereof, the apparatus comprises a light projector 1 and an associated condenser 2 for producing a concentrated narrow slit or ribbon of light 3.

The ribbon of light 3 is projected onto a rotating drum 4 which tangentially supports twenty outwardly reflection plane slivered mirrors 5, each of which is 1 inch in axial length and three forths of an inch in width. The drum 4 is fixedly mounted upon a shaft 6 carrying a pulley 7 driven by a belt 8 (see FIG. 3), coupled to the pulley 9 of an electric motor 10, the drum 4, electric motor 10, and associated mechanism being mounted within a casing 15 having an aperture 16 permitting entry of the ribbon of light 3 through the casing 15 to the mirror carrying drum 4.

As the ribbon of light 3 impinges upon each of the rotating mirrors 5, it is reflected downwardly through an aperture 17 in the floor of the casing 15 to three plane silvered mirrors 18, 19 and 20, thereby providing a repetitive scanning ribbon of light 3a.

The reflected ribbon of light 3a is further reflected from the mirrors 18, 19 and 20 which are angularly mounted within a vertically disposed column 21 located below the casing. A rotating table 22 (only shown in part and by interrupted lines in FIGS. 1 and 3) encircles the column 21. The column 21 has a vertical slot 23 permitting exit of the further reflected ribbon of light 3b from the column 21. It will be appreciated that for example due to the relative disposition of the mirrors 18, 19 and 20 that a ribbon of light 3b when projected from the top of the mirror 19 will in fact be deflected at a greater angle to the horizontal than the beam 3b as it left the bottom of the mirror 18. The inclination of each of the mirrors 18, 19 and 20 to the vertical axis of the column 21 is so arranged as to ensure that the spot beam of light which is subsequently produced, impinges on a translucent container at the most effective angle of incidence. It will be appreciated that internal reflection of light within the container may cause errors in response. Further, it is important to ensure that critical areas of the container are sufficiently scanned and hence an overlap during the vertical scan may be desirable.

Referring to FIG. 3, photosensors 45, conventionally mounted on lead screws 46 and 47, project into the column 21 through a slit 48. The photosensors 45 are operatively connected to the control apparatus as will be described hereinafter. The photosensors 45 are so positioned that they intercept the outer edges of the scanning ribbon of light 3b reflected from the plane mirrors 18, 19 and 20. It will be appreciated that the vertical positions of the photosensors 45 on the column 21 are adjusted by the lead screws 46 and 47.

Supported by the rotating table 22 is a vertical masking member 25 having a vertical slit 25 (shown in three positions in FIG. 4), which serves to occlude all but a portion of the repetitive ribbon of light 3b thereby concentrating the latter into a narrow spot beam of light 3c which traverses through an angle of 20° in the horizontal plane (see FIG. 4) as the table 22 and slit 26 are rotated. Thus, the concentrated spot beam of light, hereinafter referred to as the scanning beam 3c, scans through an angle in a vertical plane and moves through an angle in a horizontal plane. It will, of course, be understood that the position of the slit 26 relative to a bottle 27 remains constant i.e. in the centre position shown in FIG. 4.

The bottle 27 to be inspected is carried around the periphery of the rotating table 22 by fingers (not shown) serving to press the bottle 27 against rotating rollers 28 which revolve the bottle 27 as it passes through the scanning zone penetrated by the concentrated scanning beam 3c, the latter being focussed substantially on the axis of the bottle 27. Light passing through the bottle 27 is collected by a light collection apparatus, indicated generally by the reference numeral 30, associated with a photo-multiplier 34 which feeds a signal to a control circuit. The light collection apparatus 30 will be described in more detail below.

Referring to FIGS. 4 and 5, there is illustrated the light collection apparatus 30 which includes a number of fiber optic elements 31 mounted in a matrix arrangement of the front surface of a platform 32. The fiber optic elements 31 are mounted in the form of a regular square matrix of side length D, part of such a matrix is shown in FIG. 5. The other ends of the fiber optic elements 31 taken together to form a bundle 33, the end face of which is suitably shaped, optically polished and optically coupled to a photosensor element 34, namely, a photo-multiplier tube. A light diffusing screen 35, in this embodiment a sheet of flashed opal glass is placed at a distance H in front of the platform 32.

As will be appreciated, the scanning beam 3c suffers refraction and reflection on passing through the bottle 27 but for ease of illustration FIG. 5 shows the scanning beam 3c as a relatively narrow beam of light falling upon the diffusing screen 35 after passing through the bottle 27.

The scanning beam 3c moves up and down and across the surface of the diffusing screen 35 and to correct a decrease in response as it approaches the edge of the screen, mirrors (not shown) may be placed at the perimeter of the platform 32 with their reflecting surfaces normal to the front surface of the platform and facing inward across the matrix of fiber optic elements 31.

The light collecting apparatus 30 described herein, consists of 247 plastic fiber optic elements, each 60 cm. long and of 0.060 in. diameter, arranged in a regular 13 × 19 matrix with 2 cm. spacing between elements. The front portions of the elements are fixed by fasteners in a suitable mounting for example in a sheet of black nylon measuring 28 cm × 40 cm × 6 mm thick which forms the platform 35.

The nylon matrix platform is mounted in a shallow sided rectangular box frame, parallel with and separated 4 cm. from a screen of flashed opal glass measuring 28 cm × 40 cm. The four inner surfaces of the mounting frame between the matrix platform and the diffusing screen have front-silvered mirrors fitted to them to provide correction of edge effects as described above. The rear portions of the plastic fiber optic elements are tightly bundled, the end face of the bundle is shaped, optically polished, and placed approximately 5 mm from the photocathode surface of a 50 mm diameter photo-multiplier tube 34.

The performance of the light collection apparatus may be adjusted by appropriate variation of the parameters such as the number, cross-sectional area and spacing of the individual fiber optic elements in the matrix, the distance between the front portions of the elements and the diffusing screen, and the diffusing characteristics of the screen itself.

The dimension H may be varied by providing simple mechanical means for moving the platform 32 towards and away from the light diffusing screen 35.

In certain applications it may be desirable for the apparatus to have a graded or locally non-uniform response to incident light. This may be achieved by suitable modification of the spacing of the fiber optic elements when of uniform cross-section in the matrix, that is to say, by making dimension D a variable depending on the location in the matrix of the elements being considered or, alternatively, by appropriately grading the cross-sectional areas of the fiber optic elements in the matrix.

In operation, the inspection apparatus according to the invention is located adjacent to or in the path of a conveyor line (not shown) carrying bottles to be inspected. Bottles to be inspected are fed to the rotating rollers 28 against which the bottles are held and rotated while the table 22 is revolving.

It will be understood that during the scanning period, the scanning beam 3c passing through the masking slit 26 continuously scans in a vertical plane and simultaneously it is caused to move in a horizontal plane by rotary movement of the masking member 25. Further, the bottle 27 is continuously rotated during transit thereof. through the scanning zone, and the scanning rate is so arranged that the entire area of the bottle is overscanned by 25%. The scanning rate and the rotation rate of the bottle are related so that there is a 10% overlap between successive scans. Should the amount of light falling upon the light collection apparatus 30 be reduced below a predetermined level by virtue of the spot or beam of light being partially or wholly obstructed or absorbed by extraneous matter in the bottle 27, the output from the photo-multiplier 34 will be reduced, thus generating an electrical rejection signal indicative of the presence of the extraneous matter in the bottle 27. The rejection signal thereby generated is fed to actuate a rejection mechanism such as described in our British Patent Specification No. 1,206,136, which diverts the bottle 27 from the return path to the conveyor line (not shown). It will be appreciated that the successful operation of the inspection apparatus according to the present invention requires that the various operations be synchronized and controlled. Some inspection apparatus functions must be synchronized with the rotation of the rotating table 22, that is to say, with the translation of the bottle 27 from the input feed through the inspection zone to the output feed. Other functions must be synchronized with or controlled by the position of the scanning beam relative to the bottle 27 being inspected. How these synchronizations and control signals are obtained and processed is described in our co-pending application Ser. No. 483,350.

I claim:

1. In an apparatus for detecting the presence of extraneous matter and/or cracks in a translucent container said apparatus including; an inspection zone, means for rotating a translucent container within the inspection zone, means for generating and vertically scanning a spot beam of light and a light collection apparatus in the inspection zone said light collection apparatus comprising:
   a platform;
   a light diffusing screen parallel to and spaced apart from the front surface of the platform; and
   a plurality of fiber optic elements, each fiber optic element having a front, intermediate and rear portion, the front portion being attached by any suitable means to the front surface of the platform in spaced relation to each other, and the rear portion of all the elements being operatively connected to a light detection means.

2. Apparatus as recited in claim 1 in which means are provided for varying the spacing between the platform and light diffusing screen.

3. Apparatus as recited in claim 1 in which light reflecting means are provided around the perimeter of the platform normal to the front surface thereof.

4. Apparatus as recited in claim 1 in which means are provided for varying the spacing of the fiber optic elements on the platform.

5. Apparatus as recited in claim 1 in which the intermediate portion of each fiber optic element is passed through an aperture in the platform and extends a convenient distance from the rear surface of the platform, the rear portion of the elements being tightly bundled together, the end face of each bundle being shaped, optically polished and optically coupled to a photosensor means.

6. Apparatus as recited in claim 2 in which light reflecting means are provided around the perimeter of the platform normal to the front surface thereof.

7. Apparatus as recited in claim 2 in which means are provided for varying the spacing of the fiber optic elements on the platform.

8. Apparatus as recited in claim 2 in which the intermediate portion of each fiber optic element is passed through an aperture in the platform and extends a convenient distance from the rear surface of the platform, the rear portion of the elements being tightly bundled together, the end face of each bundle being shaped, optically polished and optically coupled to a photosensor means.

9. Apparatus as recited in claim 3 in which means are provided for varying the spacing of the fiber optic elements on the platform.

10. Apparatus as recited in claim 3 in which the intermediate portion of each fiber optic element is passed through an aperture in the platform and extends a convenient distance from the rear surface of the platform, the rear portion of the elements being tightly bundled together, the end face of each bundle being shaped, optically polished and optically coupled to a photosensor means.

11. Apparatus as recited in claim 4 in which the intermediate portion of each fiber optic element is passed through an aperture in the platform and extends a convenient distance form the rear surface of the platform, the rear portion of the elements being tightly bundled together, the end face bundle being shaped, optically polished and optically coupled to a photosensor means.

12. Apparatus as recited in claim 1 in which the means for generating and vertically scanning the spot beam of light comprises;
   means for generating a vertically scanning slit of light, and projecting the latter towards the inspection zone; and
   a masking member containing a vertical slit being movable horizontally in the path of the scanning slit of light so as to occlude a portion of the latter and thereby resolve the vertical scanning slit light into a spot beam scanning vertically and horizontally in the scanning vertically and horizontally in the inspection zone.

13. Apparatus as recited in claim 12, in which there is provided;
   a drum adapted for rotation;
   a plurality of plane mirrors tangentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the axis of the drum;
   a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

14. Apparatus as recited in claim 2, in which the means for generating and vertically scanning the spot beam of light comprises;
   means for generating a vertically scanning slit of light, and projecting the latter towards the inspection zone; and
   a masking member containing a vertical slit being movable horizontally in the path of the scanning slit of light so as to occlude a portion of the latter and therby resolve the vertical scanning slit of light into a spot beam scanning vertically and horizontally in the inspection zone.

15. Apparatus as recited in claim 14, in which there is provided;
   a drum adapted for rotation;
   a plurality of plane mirrors tangentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the axis of the drum;
   a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

16. Apparatus as recited in claim 4, in which the means for generating and vertically scanning the spot beam of light comprises;
   means for generating a vertically scanning slit of light, and projecting the latter towards the inspection zone; and
   a masking member containing a vertical slit being movable horizontally in the path of the scanning slit of light so as to occlude a portion of the latter and thereby resole the vertical scanning slit of light into a spot beam scanning vertically and horizontally in the inspection zone.

17. Apparatus as recited in claim 16, in which there is provided;
   a drum adapted for rotation;
   a plurality of plane mirrors tangentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the axis of the drum;
   a plurality of plane mirros adjustably mounted within the column at an agle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable that theangle of incidence of the spot beam of light on the container is the optimum angle for the detection of extraneous matter and cracks.

18. Apparatus as recited in claim 17, in which the means for generating and vertically scanning the spot beam of light comprises:
   means for generating a vertically scanning slit of light, and projecting the latter towards the inspection zone; and
   a masking member containing a vertical slit being movable horizontally in the path of the scanning slit of light so as to occulde a portion of the latter and thereby resolve the vertical scanning slit of light into a spot beam scanning vertically and horizontally in the scanning vertically and horizontally in the inspection zone.

19. Apparatus as recited in claim 18, in which means is provided for scanning the spot beam of light vertically and horizontally in the inspection zone which means comprises;
   means for generating a vertically scanning slit of light and projecting the latter towards the inspection zone; and
   a masking member containing a vertical slit being movable horizontally in the path of the scanning slit of light so as to occlude a portion of the latter and thereby resolve the vertical scanning slit of light into a spot beam scanning vertically and horizontally in the inspection zone.

* * * * *